(12) United States Patent
Mascarell et al.

(10) Patent No.: US 11,028,441 B2
(45) Date of Patent: Jun. 8, 2021

(54) IL-10 AS A PREDICTIVE BIOMARKER OF RESPONSIVENESS TO HOUSE DUST MITE ALLERGEN IMMUNOTHERAPY

(71) Applicant: STALLERGENES, Antony (FR)

(72) Inventors: Laurent Mascarell, Paris (FR); Véronique Bodo, Palaiseau (FR); Philippe Moingeon, Antony (FR); Vincent Lombardi, Antony (FR); Claire Gueguen, Reading (GB)

(73) Assignee: STALLERGENES, Antony (FR)

( * ) Notice: Subject to any disclaimer, the term of this patent is extended or adjusted under 35 U.S.C. 154(b) by 147 days.

(21) Appl. No.: 16/069,332

(22) PCT Filed: Jan. 13, 2017

(86) PCT No.: PCT/EP2017/050729
§ 371 (c)(1),
(2) Date: Jul. 11, 2018

(87) PCT Pub. No.: WO2017/121883
PCT Pub. Date: Jul. 20, 2017

(65) Prior Publication Data
US 2019/0024177 A1 Jan. 24, 2019

(30) Foreign Application Priority Data

Jan. 13, 2016 (EP) ..................... 16305026

(51) Int. Cl.
| | | |
|---|---|---|
| *C12Q 1/68* | (2018.01) | |
| *C12Q 1/6883* | (2018.01) | |
| *G01N 33/68* | (2006.01) | |
| *A61K 39/35* | (2006.01) | |
| *A61K 39/00* | (2006.01) | |

(52) U.S. Cl.
CPC ............ *C12Q 1/6883* (2013.01); *A61K 39/35* (2013.01); *G01N 33/6863* (2013.01); *A61K 2039/54* (2013.01); *C12Q 2600/106* (2013.01); *C12Q 2600/158* (2013.01); *G01N 2333/54* (2013.01); *G01N 2333/5428* (2013.01); *G01N 2800/24* (2013.01); *G01N 2800/52* (2013.01)

(58) Field of Classification Search
None
See application file for complete search history.

(56) References Cited

FOREIGN PATENT DOCUMENTS

WO     2012137180 A2     10/2012

OTHER PUBLICATIONS

Jabbari et al; J Allergy Clin Immunol; Feb. 2013, abstract.*
Lin et al; International Journal of Pediatric Otorhinolaryngology; vol. 77, pp. 1345-1349, 2013.*
B. Michaud et al, "Quantification of circulating house dust mite-specific IL-4 and 1L-13 secreting T cells correlates with rhinitis severity in asthmatic children and varies with the seasons", Clinical & Experimental Allergy, pp. 222-230, vol. 44. No. 2 (Jan. 2014).
Barberi S et al, "Immune Response to Sublingual Immunotherapy in Children Allergic to Mites", Journal of Biological Regulators and Homeostatic Agents, pp. 627-634, vol. 25, No. 4 (Oct. 2011).
Ciprandi G et al: "The practical role of serum allergen-specific IgE as potential biomarker for predicting responder to allergen immunotherapy", Expert Review of Clinical Immunology, pp. 321-324, vol. 10, No. 3 (Mar. 2014).
Greenbaum D et al., "Comparing Protein Abundance ANO MRNA Expression Levels on a Genomic Scale" Genome Biology, pp. 117, vol. 40, No. 9 (Jan. 2003).
Shamji M H et al: "Predictive biomarkers of clinical efficacy of allergen-specific inmunotherapy: How to proceed", Immunotherapy 2013 Future Medicine Ltd, pp. 203-206, vol. 5, No. 3 (2013).
V Baron-Bodo et al, "In serch of biological markers for allergy immunotherapy", Scientific Matters, pp. 9-11 (Jan. 2010).
Wei Wang et al, "Effect of house dust mite inmunotherapy on interleukin-10-secreting regulatory T cells in asthmatic children" Chinese Medical Journal, pp. 2009-2104 (Aug. 2010).

* cited by examiner

*Primary Examiner* — Jehannie S Sitton
(74) *Attorney, Agent, or Firm* — Browdy and Neimark, PLLC (57) ABSTRACT

The present invention concerns the use of IL-10 as a biological marker for predicting the responsiveness of a house dust mite allergic patient to house dust mite allergen immunotherapy.

4 Claims, 4 Drawing Sheets

Specification includes a Sequence Listing.

IL-10 AS A PREDICTIVE BIOMARKER OF RESPONSIVENESS TO HOUSE DUST MITE ALLERGEN IMMUNOTHERAPY

The present invention concerns the use of interleukin 10 (hereinafter "IL-10") as a biological marker for predicting the responsiveness of a house dust mite patient to house dust mite allergen immunotherapy.

Allergy is a major and growing health concern around the world. As societies become more affluent and reduce the incidence of contagious disease, the prevalence of allergic disease increases. Finding effective treatments for allergy, both preventive and therapeutic, is a growing challenge for today's healthcare industry. Traditionally, management of allergy has concentrated on alleviation of symptoms, using antihistamines and medications which relieve allergic symptoms including nasal congestion, dermatitis and asthma, such as decongestants, creams, anti-inflammatories and bronchodilators. Allergen avoidance is another strategy for allergy management, but this is often difficult or impossible, particularly in the case of pervasive allergens such as pollen. A third alternative is specific allergy vaccination, or allergen immunotherapy (AIT), in which patients are inoculated with the allergen causing the allergy in order to obtain an improvement in the patient's immune status. This kind of treatment has the advantage of altering the course of the illness to prevent the manifestation of symptoms, rather than simply alleviating symptoms.

Injective immunotherapy (subcutaneous immunotherapy or SCIT) was first reported in 1911 and has been used in clinical practice since the 1970s. However, the invasive nature of the therapy, requiring regular clinician visits, and problems with side effects—including in rare cases anaphylaxis and death—have impacted its uptake as a treatment of allergy. Immunotherapy via administration of allergen to mucosa, such as the oral mucosa of the mouth and gut, has also been explored. Sublingual immunotherapy (SLIT), in which vaccine is administered underneath the tongue and absorbed via the sublingual mucosa, is a well-established alternative to injective immunotherapy. SLIT has been shown to be comparable to SCIT in terms of efficacy and has a superior safety profile. It is now generally preferred to SCIT due to the less invasive nature to the technique and the lower risk of side effects, as the occurrence of harmful side effects from SLIT is relatively low. However, the expense of the treatment is still a major factor in slowing down the uptake of SLIT.

Patients' eligibility to AIT is currently based on anamnesis and the determination of IgE reactivity to a specific allergen by skin prick or in vitro testing. However, patient selection would greatly benefit from the identification of biomarkers predicting the likelihood of clinical improvement following AIT (Senna et al. Curr Opin Allergy Clin Immunol 11, 375-380 (2011); Shamji, et al. Immunotherapy 5, 203-206 (2013)).

The international patent application WO 2012/137180 has described that Fetuin-A, beta-2 glycoprotein 1, Antithrombin-III, MCP-1 and Eotaxin constitute predictive biomarkers of responsiveness of a patient to immunotherapy.

However, there is a need for further biological parameters measured before AIT allowing distinguishing patients who subsequently benefit from AIT from those who are non-responders.

IL-10 expression has traditionally been associated with the induction of tolerance further to immunotherapy. Accordingly IL-10 has been suggested as a potential follow-up biomarker of AIT efficacy based on several exploratory studies (see for instance Akdis et al. J Clin Invest 102, 98-106 (1998)). However, although some studies reported that IL-10 producing regulatory B and T cells specific for allergens are increased in the course of AIT or under natural allergen exposure (Jutel et al. J Immunol 154, 4187-4194 (1995); Jutel et al. Eur J Immunol 33, 1205-1214 (2003); Francis et al. J Allergy Clin Immunol 111, 1255-1261 (2003); Akdis et al. J Exp Med 199, 1567-1575 (2004); Bohle et al. J Allergy Clin Immunol 120, 707-713 (2007); van de Veen et al. J Allergy Clin Immunol 131, 1204-1212 (2013)), others including our group did not observe such IL-10 alteration in the patient's blood during AIT (Dehlink et al. Clin Exp Allergy 36, 32-39 (2006); Bonvalet et al. Clin Exp Allergy 42, 1745-1755 (2012)).

Furthermore, the fact that a biomarker has relevance as follow-up biomarker for efficacy of immunotherapy does not entail any conclusion on its role as predictive biomarker, and vice versa.

The present application provides evidence for high levels of IL-10 in samples, collected before specific AIT, from house dust mite allergic patients exhibiting clinical responses, when compared with non-responders. Accordingly, measuring IL-10 expression can be used as a method for predicting responsiveness of house dust mite allergic patients to AIT.

SUMMARY OF THE INVENTION

The invention relates to a method for predicting responsiveness to immunotherapy of a patient allergic to house dust mite, which method comprises measuring the level of expression of IL-10 in a biological sample from said patient, wherein said biological sample is taken before the commencement of immunotherapy, and wherein said immunotherapy comprises administration of a house dust mite allergen to said patient in order to treat house dust mite allergy.

The invention also relates to a method for selecting a house dust mite allergic patient for immunotherapy, which method comprises the steps of:

a) detecting the level of expression of IL-10 in a biological sample from said patient;
b) comparing said level of expression with a control;
c) selecting or rejecting said patient for immunotherapy based on the comparison with the control;

wherein said biological sample is taken before the commencement of immunotherapy, and wherein said immunotherapy comprises administration of an house dust mite allergen to said patient in order to treat house dust mite allergy.

In another aspect, the invention relates to a house dust mite allergen for use for immunotherapy of house dust mite allergy in a patient selected for immunotherapy, comprising selecting the patient for immunotherapy by implementing the method for selecting patient of the invention.

The invention further provides a method of treating a house dust mite allergic patient by immunotherapy, which comprises:

a) detecting the level of expression of IL-10 in a biological sample from said patient taken before the commencement of immunotherapy;
b) comparing said level of expression with a control;
c) selecting or rejecting said patient for immunotherapy based on the comparison with the control;

wherein said biological sample is taken before the commencement of immunotherapy; and d) administering a house dust mite allergen to said patient selected for immunotherapy in order to treat allergy to said allergen.

According to the invention, measuring the level of expression of IL-10 is performed by measuring abundance of IL-10 mRNA.

DESCRIPTION OF THE INVENTION

The invention provides a method to select house dust mite allergic patients eligible for AIT based on IL-10 levels. Using this method, Average Adjusted Symptom Scores (AASS) measured after receiving the active treatment were much lower in patients presenting a high level of IL-10 expression at baseline when compared to AASS in the whole cohort of unselected patients.

Immunotherapy

"Immunotherapy" is intended to mean a treatment of disease by inducing, enhancing, or suppressing an immune response by administration of substances (e.g. allergens).

"Therapy", "therapeutic", "treatment" or "treating" include reducing, alleviating or inhibiting or eliminating the causes of a disease or pathological conditions (e.g. allergy), as well as treatment intended to reduce, alleviate, inhibit or eliminate symptoms of said disease or pathological condition. These terms may include preventive treatment which is intended to, or has the effect of preventing onset of the disease or pathological condition, or reducing, alleviating, inhibiting or eliminating future symptoms. They may also include treatment of ongoing symptoms.

"Allergy", or "type 1 hypersensitivity", is a condition characterized by production of allergen-specific IgE in response to a specific allergen, usually a protein. Clinical manifestations and symptoms of allergy may include nasal congestion, nasal pruritus, ocular pruritus, tearing, rhinorrhoea, sinusitis, rhinitis, sneezing, wheezing, conjunctivitis, dermal itching, dermatitis, skin irritation, hives, shortness of breath, repetitive cough and asthma.

In relation to allergy, immunotherapy comprises administering a house dust mite allergen to the patient in order to treat house dust mite allergy of the patient, i.e. reducing current or future immune response, such as an allergen-specific IgE response and/or histamine release by mastocytes and/or granulocytes induced by the allergen, and/or manifestation of clinical symptoms of allergy. Immunotherapy is conventionally carried out by administering repeatedly a monodose or incremental doses of an allergen to a patient in need thereof, thereby resulting in an adaptive immune response of the patient who becomes desensitised to the allergen.

In some embodiments, immunotherapy comprises administration of allergen to a mucosal surface, such as a sublingual, oral, nasal, buccal, ocular, rectal, vaginal, pulmonary or ear surface. In particular, immunotherapy is preferably sublingual immunotherapy. Alternatively, in other embodiments immunotherapy comprises administration via a parenteral route, such as intralymphatic, subcutaneously or intravenously, for example via injection, or via alternative routes such skin immunisation e.g. transdermal or epicutaneous administration.

An allergen is a substance, usually a protein, which elicits the production of IgE antibodies in predisposed individuals. Allergens include house dust mite allergens.

For instance, an allergen may be selected from the group consisting of a protein allergen of the genus *Dermatophagoides*.

Examples of various known protein allergens derived from the above-identified genus include: *Dermatophagoides* (*pteronyssinus* or *farinae*) Der p 1; Der p 2; Der p 23, Der f 1; Der f 2.

The "allergen" used for immunotherapy may be a single allergenic substance or a mixture of such substances, for example a mixture of allergens. In such case, the mixture may comprises allergens having equimolar amounts or with varying amounts within ratio preferably up to 1:2, 1:3, 1:4, 1:5, 1:6, 1:7, 1:8, 1:9, 1:10, 1:15, 1:20. It may be an allergen extract. The allergen extract may be a partially or fully purified allergen extract. The allergen extract may be a modified (e.g. allergoids) or a non-modified allergen extract. The allergen may also be a recombinant protein, a fusion protein, a mutant, or peptide derived there from. The allergen may further be an hypoallergen, such as an allergoid (chemically modified form of a naturally occurring allergen which has been chemically modified for example by aldehydation) or a mutant with reduced allergenicity, or peptide derived therefrom. For example, the allergen administered for immunotherapy may be a house dust mite extract from one or several genera of house dust mites, such as mites of *Dermatophagoides* genus. The allergen may be administered in conjunction with an adjuvant and/or a vector system.

The composition used for immunotherapy may be in liquid phase, solid phase or a combination of both such as adsorbed vaccine.

It may comprise for instance a total amount of 0.01-10, 000 µg, preferably 0.01-1000 µg, preferably 0.1-500 µg of allergens, more particularly of major allergens, more particularly of each of group I and/or group II house dust mite allergens.

The allergen content of the composition may be expressed in term of biopotency (allergenic activity as measured in vivo and/or in vitro) for which there is currently no internationally accepted standardised method. The bio-potency of a given extract mostly depends on the content of relevant allergens in the extract, which content varies with the biological source material. Different units have been developed such as IR (index of reactivity), BAU (Bioequivalent Allergen Units), AU (Allergy Units), SQ-Units (Standardised Quality Units). Index of Reactivity or IR are established on the basis of Stallergenes' biopotency IR standardised method. The IR can be determined by means of an immunoassay such as inhibition ELISA assay. 100 IR containing grass pollen extracts equal around 3000 BAU. BAU or Bioequivalent Allergen Units is the biopotency units established on the basis of the FDA requirements described in "Methods of the Allergenics Products Testing Laboratory", October 1993, Docket No. 94N-0012 at p. 15. As to its potency, the composition used for immunotherapy may comprise for instance a total value of 0.01-10,000 IR, preferably 0.1-1,000 IR, preferably 1-500 IR, preferably 100-300 IR. In an embodiment, the immunotherapy comprises administration of an allergen extract of at least one *Dermatophagoides* species, preferably a mixture of allergen extracts of *D. pteronyssinus* and *D. farinae*, more preferably a mixture of allergen extracts of *D. pteronyssinus* and *D. farinae* having similar amount of each extract or with varying amounts within ratio preferably up to 1:2, 1:3, 1:4, 1:5, 1:6, 1:7, 1:8, 1:9, 1:10, 1:15, 1:20. In another embodiment, the mixture of extracts of *D. pteronyssinus* and *D. farinae* has equimolar amounts of major allergens or with varying amounts within ratio preferably up to 1:2, 1:3, 1:4, 1:5, 1:6, 1:7, 1:8, 1:9, 1:10, 1:15, 1:20. In a further embodiment, the mixture of extracts of *D. pteronyssinus* and *D. farinae* has similar allergenicity from each extract, each having preferably a potency of 0.01-10,000 IR, preferably 0.1-1,000 IR, preferably 1-500 IR, preferably 100-300 IR, or with varying ratio preferably up to 1:2, 1:3, 1:4, 1:5, 1:6, 1:7, 1:8, 1:9, 1:10, 1:15, 1:20. As a more preferred embodiment, such compositions are formulated in a tablet such as a fast release tablet.

"Response" of a patient to treatment indicates that the patient manifests a reduction in the clinical symptoms. Clinical symptoms may be assessed over the course of treatment, i.e. symptoms before treatment may be compared to symptoms during and after treatment. Alternatively, a reduction in symptoms may be determined by comparison to a baseline level established before treatment. Concerning allergy, this approach is particularly useful where, for example, immunotherapy is carried out in patients not currently experiencing symptoms, as may be the case for seasonal grass pollen allergy sufferers, who may be treated before the pollen season. Symptoms may be assessed by standard methods, such as patient self-assessment or record of the amount of medication required. The degree of a patient's response to treatment may be assessed by measuring the degree of reduction of severity in symptoms.

A "responder" subject as defined herein is a subject who responds to immunotherapy or vaccine administration with an improvement in clinical symptoms, preferably a statistically significant improvement as compared to patients receiving placebo or no treatment. Preferably, a responder subject will demonstrate at least 10%, 11%, 12%, 13%, 14%, 15%, 16%, 17%, 18%, 19%, 20%, 25%, 30%, 35% or 50% improvements of clinical symptoms. As another preferred embodiment, a responder subject will demonstrate an improvement in clinical symptoms which is greater than the average or median improvement seen in a random sample of subjects.

A "non-responder" subject is a subject who does not manifest any improvement in clinical symptoms following immunotherapy or vaccine administration, or who demonstrates a non-statistically significant improvement in symptoms, or who demonstrate less than 10%, 11%, 12%, 13%, 14%, 15%, 16%, 17%, 18%, 19%, 20%, 25%, 30%, 35% or 50% improvement of clinical symptoms, or who demonstrates an improvement in clinical symptoms which is less than the average or median improvement seen in a random sample of subjects.

For example, improvement in clinical symptoms for type 1 hypersensitivity or allergy may be detected by:
- a reduction in the frequency or severity of nasal congestion, nasal pruritus, ocular pruritus, tearing, rhinorrhoea, sinusitis, rhinitis, sneezing, wheezing, conjunctivitis, dermal itching, dermatitis, skin irritation, hives, shortness of breath, repetitive cough and asthma, and/or reduction in the uptake of known relief medication such as anti-histaminic, corticosteroids, bronchodilatator agents or antileukotriene agents.
- An improvement of a lung function test such as air flow debit, flow volume, FEV1 (forced expiratory volume in 1 second),
- A reduction in inflammatory parameters such as NO
- A reduction in the reactivity to an allergen challenge such as, intranasal, intraconjunctivial, Intrabronchial, skin prick test Moreover, improvement of clinical symptoms may also be demonstrated on the basis of a combination thereof such as Symptoms Score (e.g. Rhinoconjunctivitis Total Symptom Score (RTSS) or Average Rhinoconjunctivitis Total Symptom Score (ARTSS)), Medication Score (e.g. Rescue Medication Score (RMS) or Average Rescue Medication Score (ARMS)), Combined Scores (e.g. Combined Symptoms Score (CS), Average Combined Symptoms Score (ACS), Average Adjusted Symptoms Score (AASS or AdSS)) (See Clark J. et al., Allergy 2007: 62: 1023-1028; Pfaar et al., Allergy 2014: 69: 854-867), ACT (Asthma Symptoms Score), ACQ (Asthma Control Questionnaire), GINA asthma management guide (Global Initiative for Asthma).

Patient

The patient is preferably a mammal, such as a rodent, a feline, an equine, a bovine, an ovine, a canine or a primate, and is preferably a human, in particular a child, a woman, a man.

Depending on the origin of sample to be tested (e.g. a rodent, a feline, an equine, a bovine, an ovine, a canine or a primate . . . ), the person skilled in the art will easily determine which are the sequences of the homologous IL-10 mRNA or polypeptide to be detected by consulting the commonly known sequence databases and will therefore choose the means suitable for detecting these markers.

For instance, when the patient is a human, IL-10 mRNA or polypeptide is intended to mean any naturally occurring isoform of the IL-10 mRNA or protein naturally encoded by human genome, including the mRNA comprising or consisting of the sequence SEQ ID NO:1, or comprising or consisting of a sequence complementary to SEQ ID NO: 2, or the protein having an amino acid sequence corresponding to the sequence SEQ ID NO:3 or SEQ ID NO:4.

"Patient" includes any individual allergic to house dust mite who is a candidate for allergen immunotherapy.

For allergen immunotherapy, in most cases, the patient is an individual who has, or has had at any time in the past, clinical symptoms of house dust mite allergy and/or sensitization to an allergen and/or an allergen-specific IgE response, or an individual at risk of developing such symptoms. Sensitisation to an allergen may be assessed by detecting IgE directed against allergen(s) from this source in the serum of the patient or by skin testing with a preparation containing the corresponding allergen(s). The allergen include a house dust mite allergen.

According to the present invention, the patient has house dust mite allergy, in particular allergy to a *Dermatophagoides* allergen. In this embodiment, the immunotherapy uses at least one house dust mite allergen, in particular a house dust mite allergen extract. In particular, the immunotherapy may comprise administration of a mixture of allergen extracts of *D. pteronyssinus* and *D. farinae*, more preferably a mixture of allergen extracts of *D. pteronyssinus* and *D. farinae* having similar amount of each extract or with varying amounts within ratio preferably up to 1:2, 1:3, 1:4, 1:5, 1:6, 1:7, 1:8, 1:9, 1:10, 1:15, 1:20. In another embodiment, the mixture of extracts of *D. pteronyssinus* and *D. farinae* has equimolar amounts of major allergens or with varying amounts within ratio preferably up to 1:2, 1:3, 1:4, 1:5, 1:6, 1:7, 1:8, 1:9, 1:10, 1:15, 1:20. In a further embodiment, the mixture of extracts of *D. pteronyssinus* and *D. farinae* has similar allergenicity from each extract, each having preferably a potency of 0.01-10,000 IR, preferably 0.1-1,000 IR, preferably 1-500 IR, preferably 100-300 IR, or with varying ratio preferably up to 1:2, 1:3, 1:4, 1:5, 1:6, 1:7, 1:8, 1:9, 1:10, 1:15, 1:20. As a more preferred embodiment, such compositions are formulated in a tablet such as a fast release tablet.

Biological Sample

The biological sample may be, without limitation, whole blood, peripheral blood mononuclear cells (PBMCs), subsets of immune cells (e.g. B and/or T cells, dendritic cells, eosinophils, innate lymphoid cells, macrophages, neutrophils, monocyte, basophils and NK cells), cell culture supernatant, body fluids (e.g. blood serum, blood plasma, lymph, breast milk, feces, mucus, saliva, sputum, urine, nasal secretion, bronchoalveolar fluid, cerebrospinal fluid), mucosal tissues, exhaled air condensate or epithelial brushing. In a particularly preferred embodiment, the biological sample is a whole blood sample.

The biological sample may be taken at a time when the patient does or does not exhibit symptoms or allergy to the allergen used for immunotherapy.

The biological sample collected from the patient may be submitted to a processing such as separation, purification, fractionation, enzymatic processing etc. . . . prior to measuring the level of expression of IL-10. Accordingly, measuring the level of expression of IL-10 can be performed directly in the biological sample, or in a fraction thereof.

Measuring the Level of Expression of IL-10

Measuring the level of expression of IL-10 can be achieved by different means.

According to the invention, the level of expression of IL-10 is determined by measuring the abundance (or quantity) of IL-10 mRNA.

Measuring quantity of IL-10 mRNA may be achieved by detecting IL-10 mRNA.

A reference sequence of human IL-10 mRNA is available for instance from the NCBI database under accession number NM_000572.2 (SEQ ID NO: 1). In an embodiment, the "IL-10 mRNA" denotes an mRNA comprising or consisting of the sequence SEQ ID NO: 1. A reference sequence of human IL-10 gDNA is available for instance from the NCBI database under accession number NG_012088.1 (version SEQ ID NO: 2). In another embodiment, the "IL-10 mRNA" denotes a mRNA comprising or consisting of a sequence complementary to SEQ ID NO: 2 or a spliced form thereof.

The level of expression of mRNAs of the marker proteins may be determined by real-time quantitative RT-PCR, using primers specific for the marker proteins to be measured. This method allows the detection of mRNA in a biological sample by generating cDNA by reverse transcription using at least one primer; amplifying the cDNA so produced using gene specific polynucleotides as sense and antisense primers and detecting the presence of the amplified cDNA by methods well known to the person skilled in the art.

Such methods may include the use of IL-10 specific probes composed of nucleic acids (DNA, RNA) complementary to the target sequence such as Taqman probes or probes labeled with radioactive isotope or chemiluminescent substrates. Possible standards include Actin-β, Glyceraldehyde-3-phosphate dehydrogenase (GAPDH), hypoxanthine phosphoribosyltransferase (HPRT), β2-microglobulin, 18S rRNA.

Other methods such as high throughput sequencing are also applicable.

As further described, the level of expression of IL-10 can be determined by measuring the abundance (or quantity) of IL-10 polypeptide.

A reference sequence of human IL-10 polypeptide is available for instance from UniProtKB/Swiss-Prot database under accession number P22301 (entry version of 1 Aug. 1991, SEQ ID NO: 1). The complete IL-10 sequence (pre-protein) consists of 178 amino acids, and comprises a signal peptide spanning amino acids 1-18, and a secreted mature polypeptide spanning amino acids 19-178. As used herein, "IL-10 polypeptide" includes all isoforms of IL-10 proteins, of which post-translationally modified forms such as glycoforms. Accordingly, in an embodiment the "IL-10 polypeptide" denotes a polypeptide consisting of the sequence SEQ ID NO: 3. More preferably, "IL-10 polypeptide" denotes a polypeptide consisting of the sequence SEQ ID NO: 4.

Measuring quantity of IL-10 polypeptide may be achieved by measuring the IL-10 polypeptide, or a degraded fragment thereof (for instance if mass spectrometric techniques are to be used for measurement). Said degraded fragment may result from proteolytic treatment of the IL-10 polypeptide with a protease. The sequence of said degraded fragment can be predicted by the person having skills in the art in an obvious manner based on the knowledge of the IL-10 polypeptide sequence and by employing a protease with a defined proteolytic pattern such as trypsin.

The level of expression of IL-10 polypeptide may be determined by gel electrophoresis (SDS-PAGE), in particular two-dimensional gel electrophoresis (2D-PAGE), carried out on the biological sample or a protein-containing extract thereof. 2D-PAGE is a well-established technique in which proteins are first separated in one dimension by isoelectric focusing and further separated by SDS-PAGE along a second dimension. Protein expression may be analysed by visualization of labeled proteins, or by Western blotting and immune detection. Protein quantification by 2D-PAGE is usually carried out by 2D-DiGE, in which proteins from a control sample and the test sample are labelled with different dyes. The dyes are mass- and charge-matched so the labeled proteins migrate to the same position on the gel, allowing quantification to be carried out within a single gel.

The level of expression of IL-10 polypeptide may also be measured by mass analysis, such as mass spectrometry. Qualitative and quantitative mass spectrometric techniques are known and used in the art. A quantitative LC-MS/MS can also be used.

An antibody, aptamer or DARPin which binds specifically to IL-10 polypeptide may also be used for measuring the level of expression of IL-10 polypeptide.

According to an embodiment, the level of expression of IL-10 polypeptide is measured using an antibody which binds to IL-10, preferably which is specific to IL-10, for example a monoclonal or polyclonal antibody, an antibody variant or fragments such as a single chain antibody, a diabody, a minibody, a single chain Fv fragment (sc(Fv)), a Sc(Fv)$_2$ antibody, a Fab fragment or a F(ab')$_2$ fragment, a V$_H$H antibody or a single domain antibody. The antibody may be mono-, bi-, tri- or multivalent. The antibody may be immobilized on a solid support. Antibodies may be used to determine IL-10 polypeptide expression in a range of immunological assays including competitive and non-competitive assay systems using techniques such as Western blotting, radioimmunoassay such as RIA (radio-linked immunoassay), ELISA (enzyme linked immunosorbent assay), "sandwich" immunoassays, immunoprecipitation assays, immunodiffusion assays, agglutination assays, complement-fixation assays, immunoradiometric assays, fluorescent immunoassays, e.g. FIA (fluorescence-linked immunoassay), chemiluminescence immunoassays, electrochemiluminescence immunoassay (ECLIA), protein A immunoassays and Luminescent Oxygen Channeling Assays.

According to another embodiment, the level of expression of IL-10 polypeptide is measured using a protein-specific aptamer. An aptamer is an oligonucleotide or peptide molecule that binds specifically to a specific target molecule. As an oligonucleotide, it can be a short single-stranded DNA or RNA (ssDNA or ssRNA). As a short peptide it consists of a variable peptide loop attached at both ends to a protein scaffold. Methods for making aptamers are well known in the art, such as the Systematic Evolution of Ligands by Exponential Enrichment (SELEX) for oligonucleotide aptamers or the yeast two-hybrid system for peptide aptamers. Such aptamers may preferably be labeled in order to allow the detection of a protein-ligand interaction. A nanotechnology-based assay could also be used.

According to a further embodiment, the level of expression of IL-10 is measured using a protein specific DARPin. A DARPin (designed ankyrin repeat proteins) is a genetically engineered polypeptide generally comprising four to five ankyrin repeat motifs and exhibiting highly specific and high-affinity target protein binding.

Predicting Responsiveness of the Patient Based on the Level of Expression of IL-10

The expression of the IL-10 biomarker in a patient biological sample is compared with a control. This control may be a control standard value and/or may consist of the expression of said IL-10 mRNA or polypeptide in a control sample, for instance a control sample of the same nature as the biological sample.

The method for predicting responsiveness of a patient allergic to house dust mite to immunotherapy typically comprises the steps of:

a) detecting the level of expression of IL-10 (IL-10 mRNA or IL-10 polypeptide, or a fragment thereof) in the biological sample of the patient;

b) comparing said level of expression of IL-10 with a control;

c) identifying said patient as likely to be a responder or non-responder to immunotherapy based on the comparison with the control.

According to an embodiment, step c) of identifying said patient as likely to be a responder or non-responder to immunotherapy is performed by:

(i) determining that the patient is likely to be a responder to immunotherapy if the control is derived from a responder subject, or group of responder subjects, known to respond to said immunotherapy, and if a level of expression of said IL-10 in the patient sample is equal to or greater than the level of expression in the control; or (ii) determining that the patient is likely to be a responder to immunotherapy if the control is derived from a non-responder subject, or group of non-responder subjects, and if the level of expression of said IL-10 in the patient sample is greater than the level of expression in the control; or (iii) determining that the patient is likely to be a responder to immunotherapy if the control is derived from a randomly selected group of subjects, and if a level of expression of said IL-10 in the patient sample is equal to or greater than the level of expression in the control.

In embodiments wherein the abundance of the IL-10 mRNA or fragment thereof is measured, the control preferably consists of a value of the abundance of the IL-10 mRNA or fragment thereof, expressed in copy numbers per million copies of β-actin mRNA, as determined by qRT-PCR, which is established by (i) defining a threshold value for the percentage of AASS improvements, (ii) defining a threshold value of sensitivity of the test and (iii) determining the corresponding threshold value of IL-10 mRNA abundance or a fragment thereof. In other embodiments, instead of determining a threshold value of sensitivity of the test in step (ii), a threshold value of specificity may be selected. In further embodiments, both a threshold value of sensitivity and specificity in step (ii) may be selected. As a more preferred embodiment, any of the copy numbers in a biological sample defined in tables 1, 2 and 3 can be selected.

Method for Selecting a Patient for Immunotherapy

In said method, the expression of the IL-10 biomarker in a house dust mite allergic patient biological sample may also be compared with a control standard value and/or with the expression of said IL-10 mRNA or polypeptide in a control sample, for instance a control sample of the same nature as the biological sample.

In an embodiment of the method for selecting a patient allergic to house dust mite for immunotherapy according to the invention, selecting or rejecting said patient for immunotherapy based on the comparison with the control is performed by:

(i) if the control is derived from a responder subject or group of responder subjects known to respond to said immunotherapy, selecting the patient for immunotherapy if the level of expression of said IL-10 in the patient sample is equal to or greater than the level of expression in the control;

(ii) if the control is derived from a non-responder subject or group of non-responder subjects, selecting the patient for immunotherapy if the level of expression of said IL-10 in the patient sample is greater than the level of expression in the control; or (iii) if the control is derived from a randomly selected group of subjects, selecting the patient for immunotherapy if the level of expression of said IL-10 in the patient sample is equal to or greater than the level of expression in the control.

In embodiments wherein the abundance of the IL-10 mRNA or fragment thereof is measured, the control preferably consists of a value of the abundance of the IL-10 mRNA or fragment thereof of at least any of the copy numbers defined in tables 1, 2, and 3 per million copies of β-actin mRNA, as determined by qRT-PCR.

Implementation of Immunotherapy in Patients Selected for Immunotherapy

Patients allergic to house dust mite that are selected for immunotherapy with the allergen, or predicted to be responsive to immunotherapy with the allergen, are then administered with the allergen, to treat allergy to the antigen, e.g. by reducing immune response to the allergen.

Preferably, the invention relates to an allergen for use for immunotherapy of allergy in an allergic or sensitized patient to house dust mite selected for allergen immunotherapy by a method according to the invention.

The invention further provides a method of treating a patient allergic to house dust mite by immunotherapy Throughout the instant application, the term "comprising" is to be interpreted as encompassing all specifically mentioned features as well optional, additional, unspecified ones. As used herein, the use of the term "comprising" also encompasses the embodiment wherein no features other than the specifically mentioned features are present (i.e. "consisting of") as well as the embodiment wherein features other than the specifically mentioned feature are present provided that the essential characteristics of the composition are not materially affected by their presence (i.e. "consisting essentially of").

The invention will be further illustrated in view of the following figures and examples.

FIGURES

FIG. 4: ROC curves of IL-10 mRNA abundance. ROC curves of IL-10 mRNA abundance in active group with % AASS improvement as a cut off of 16.54% (A), 25% (B) and 51.18% (C) to define responder patients and in which the controls are defined as non-responder patients (i.e. patients with a percentage of improvement in AASS lower than a threshold) (AUC: area under the ROC curve).

EXAMPLES

In order to identify biological parameters allowing distinguishing house dust mite allergic patients, before they initiate allergen immunotherapy (AIT), who will subsequently benefit from AIT from those who are non-responders, experiments have been conducted on biological samples from patients undergoing a phase 2/3 clinical trial with house dust mite SLIT tablet.

Example 1: Study Design for Evaluation of House Dust Mite SLIT Tablet Efficacy and Safety in a Large Scale One-Year Study in Patients with Allergic Rhinitis Clinical Trial Design:
A randomized, double-blind, placebo-controlled study has been conducted to evaluate the efficacy and safety of house dust mite (HDM) tablet in adolescent and adult patients with HDM allergic rhinitis, with or without intermittent asthma. Subjects were randomized 1:1:1 to placebo or active treatment with HDM extracts at doses (expressed in Index of Reactivity [IR], the in-house standardization unit) of 300 IR or 500 IR and treated for 52 weeks.

Study Population:
The full analysis set included 927 subjects, encompassing patients receiving either 300 IR (N=315), 500 IR (N=296) and placebo (N=316) tablets.

Participants:
The main inclusion criteria were males or females; ages between 12 and 64 years; a clinical history of HDM-induced allergic rhinitis at least for 2 years; positive HDM-specific serum IgE and positive nasal provocation test.

Study Treatment and Other Medications:
Two doses of HDM tablets, 300 IR and 500 IR, were administered in the active treatment groups. Active tablets contain a 1:1 mixture of standardized extracts of *D. pteronyssinus* and *D. farinae*. Placebo tablets were administered to the placebo group.

Subjects were instructed to use RM (Rescue Medication) if symptoms were intolerable or interfered with daily activities, and in a step-wise manner, at step 1: oral or ophthalmic antihistamine, step 2: nasal corticosteroid, step 3: oral or ophthalmic antihistamine with nasal corticosteroid.

Assessments:
Subjects recorded their daily nasal symptoms (0-4 for sneezing, rhinorrhea and nasal congestion, and 0-3 for nasal pruritus, total 0-15 point scale), ocular symptoms (0-4 for itchy eyes and watering eyes), interference with daily activities (0-4) and RM use, for the 2-weeks interim evaluation periods (week 8-10, 16-18, 24-26, 32-34 and 40-42) and the end of treatment evaluation period (week 44-52, primary evaluation period). Rescue medication score (RMS; range, 0-2) was assigned as 1 if a subject took oral and/or anti-histamine (Step 1), and 2 if a subject took nasal corticosteroid (Step 2). If a subject took both anti-histamine and nasal corticosteroid (Step 3), RMS of 2 was assigned.

Outcomes:
The primary efficacy endpoint was the AASS in the last last weeks of the 52-week treatment period (weeks 44-52) (Grouin et al. Clin Exp Allergy. 2011; 41:1282-8). The AASS is the average for each patient of the Adjusted Symptom Score (ASS) which is derived as follows. If a subject did not take RM on the day or previous day, the ASS equaled to the Rhinitis Total Symptom Score (RTSS). If a subject took RM on the day, the ASS on the day was equal to the RTSS of the day or the ASS of the previous day, whichever was higher, and the ASS of the next day was the RTSS on the next day, or the ASS of the day before, whichever was higher. The RTSS (range, 0-15) was the sum of the 4 rhinitis symptom scores. The Combined Score (CS; range, 0-2.875) is derived as (RTSS/4+RMS)/2.

Example 2: Identification of IL-10 as a Biomarker of AIT Efficacy

In the context of the clinical trial described in example 1, ancillary biomarker studies were conducted in HDM allergic patients receiving daily either 300 IR HDM tablets (n=75) or a placebo (n=77). In this study clinical responses were evaluated in each individual patient as percentages of improvement in Average Adjusted Symptom Score (AASS) which adjusts symptom scores for the use of rescue medication.

Methods
Patient Subgroups
The median percentages of AASS improvement in the active group after treatment was also used as a threshold to identify clinical responders, with patients exhibiting a ≥51.18% AASS improvement considered as responders, and those with a lower improvement as non-responders. Based on this threshold, 4 patient subgroups were defined, including active responders (ARs, n=38), active non-responders (ANRs, n=37), placebo responders (PRs, n=18), and placebo non-responders (PNRs, n=59).

Sample Collection
Whole blood cells were collected at baseline (Visit 2; V2) and after 2 (V6) and 12 months (V17) of AIT by using PAXgene blood RNA tubes (Qiagen), and kept frozen at −20° C. until use. All biological analyses were performed on samples coded to the operators.

RNA Isolation and Quantitative Real-Time PCR Analyses

Total RNAs, including miRNAs, were extracted with the nucleic acid purification kit (PAXgene Blood miRNA Kit) as per the manufacturer's instructions. cDNAs were synthesized using the SuperScript® VILOTM cDNA Synthesis kit (Applied Biosystems, Les Ulis, France) as per the manufacturer's instructions. The expression of IL-10 gene (IL-10-Hs00174066_m1) was assessed and compared with endogenous β-actin (Hs99999903_m1) as a control by quantitative PCR (qPCR) on a 7900HT Real-Time PCR system (Applied Biosystems) according to the manufacturer's instructions. The relative amounts of IL-10 mRNAs corresponding to the target gene in each sample were calculated in comparison with the calibrator gene, i.e. endogenous β-actin, using the following equation: $\Delta Ct=(Ct\ IL-10-Ct\ \beta$-actin). For graph analyses, the formula $(2^{-\Delta Ct})\times 10^6$ was used in order to determine copy numbers of IL-10 mRNA per million copies of β-actin mRNA.

Statistical Analyses

Statistical differences between groups and correlation analyses were performed by using Mann-Whitney and Spearman tests, respectively, with P values <0.05 considered significant.

Results

Figure 1:
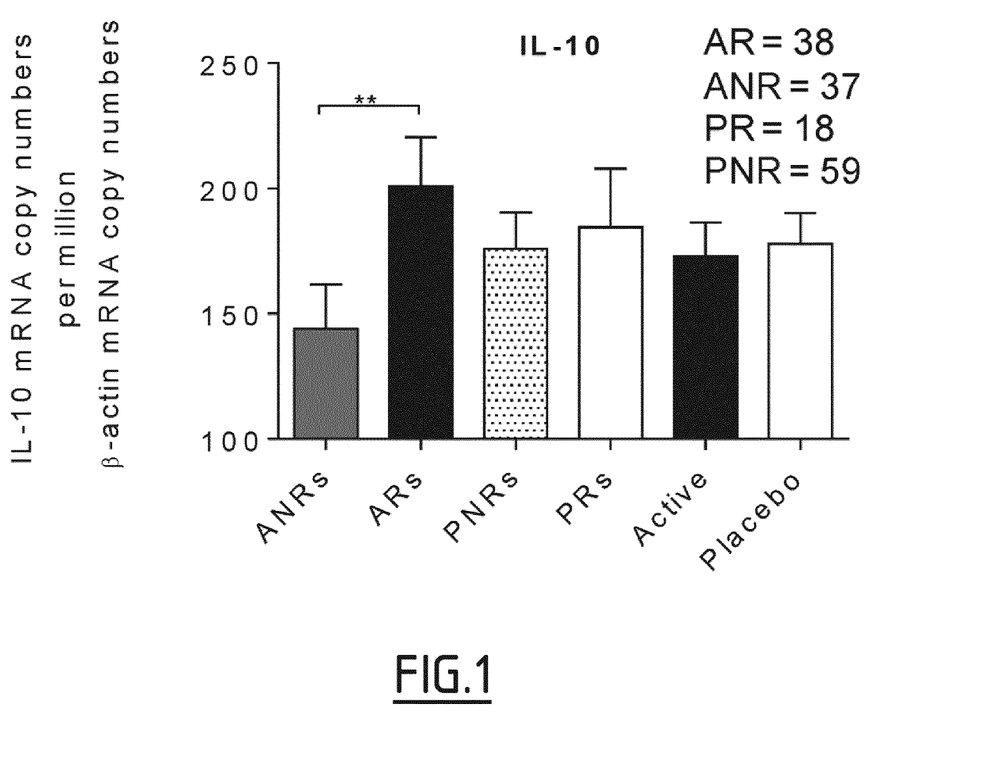
FIG. 1. Higher IL-10 mRNA levels in whole blood cells from HDM allergic patients responding to AIT. Expression of the IL-10 gene (mean±SEM) was assessed at baseline (before treatment—V2) by qPCR in whole blood cells from patients of the active and placebo groups (ARs, n=38; ANRs, n=37; PRs, n=18; and PNRs, n=59) (** P<0.01, Mann-Whitney tests). A threshold of 51.18% AASS improvement after treatment (improvement of AASS between 44-52 weeks of treatment and baseline—V17/V2) was applied to distinguish responders from non-responders.

At Baseline, IL-10 mRNA Levels are Higher in Whole Blood Cells of Clinical Responders than in Non-Responders and Significantly Correlate with Clinical Benefit within Patients from the Active Group To evaluate IL-10 as a predictive marker of clinical responses to AIT, we measured the expression of IL-10 by qPCR in whole blood cells collected before AIT (V2) from 152 HDM allergic patients receiving either a 300 IR HDM (n=75) or placebo (n=77) tablet sublingually, once a day, for 12 months. Patients were stratified in 4 subgroups (cf. Methods), including active responders (ARs; n=38), active non-responders (ANRs; n=37), placebo responders (PRs; n=18), and placebo non-responders (PNRs; n=59). As shown in FIG. 1, IL-10 mRNA levels were significantly (p<0.01) higher in ARs than in ANRs. No such differences were observed in the placebo group between PRs and PNRs and there was no potential bias since there was no differences between the active and the placebo groups (FIG. 1).

Figure 2:
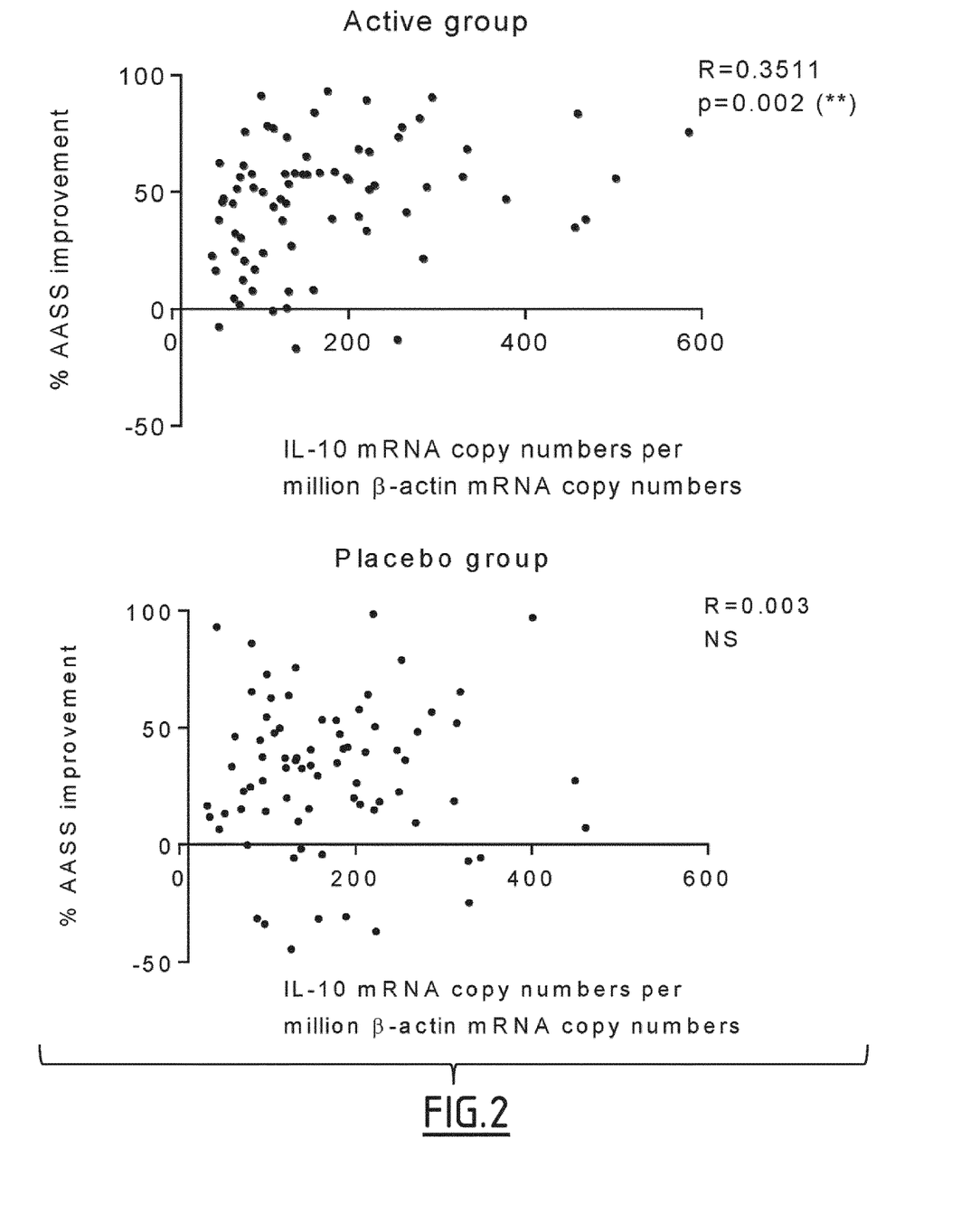
FIG. 2. IL-10 mRNA levels in whole blood cells from HDM allergic patients correlate with AIT clinical efficacy. Expression of the IL-10 gene (mean±SEM) was assessed at baseline (before treatment—V2) by qPCR in whole blood cells from patients of the active and placebo groups (Actifs=75, Placebo=77). Spearman correlations at an individual patient level of IL-10 gene levels by plotting copy numbers of IL-10 mRNA per million copies of β-actin mRNA against percentage improvements in AASS (improvement of AASS between 44-52 weeks of treatment and baseline—V17/V2) in patients from the active (upper panel) and placebo (lower panel) groups (** $p<0.01$, ns=non-significant; Spearman test).

When plotted against percentages of AASS improvement (V17/V2) for each individual patient, levels of IL-10 mRNA were significantly correlated (with a Spearman correlation R=0.3511, p=0.002) with clinical benefit within patients from the active group (FIG. 2, upper panel), whereas no such a correlation was observed in placebo-treated patients (FIG. 2, lower panel).

Selection of IL-10 High Patients Improves the Difference in Clinical Scores Between Active and Placebo Patients.

Figure 3:
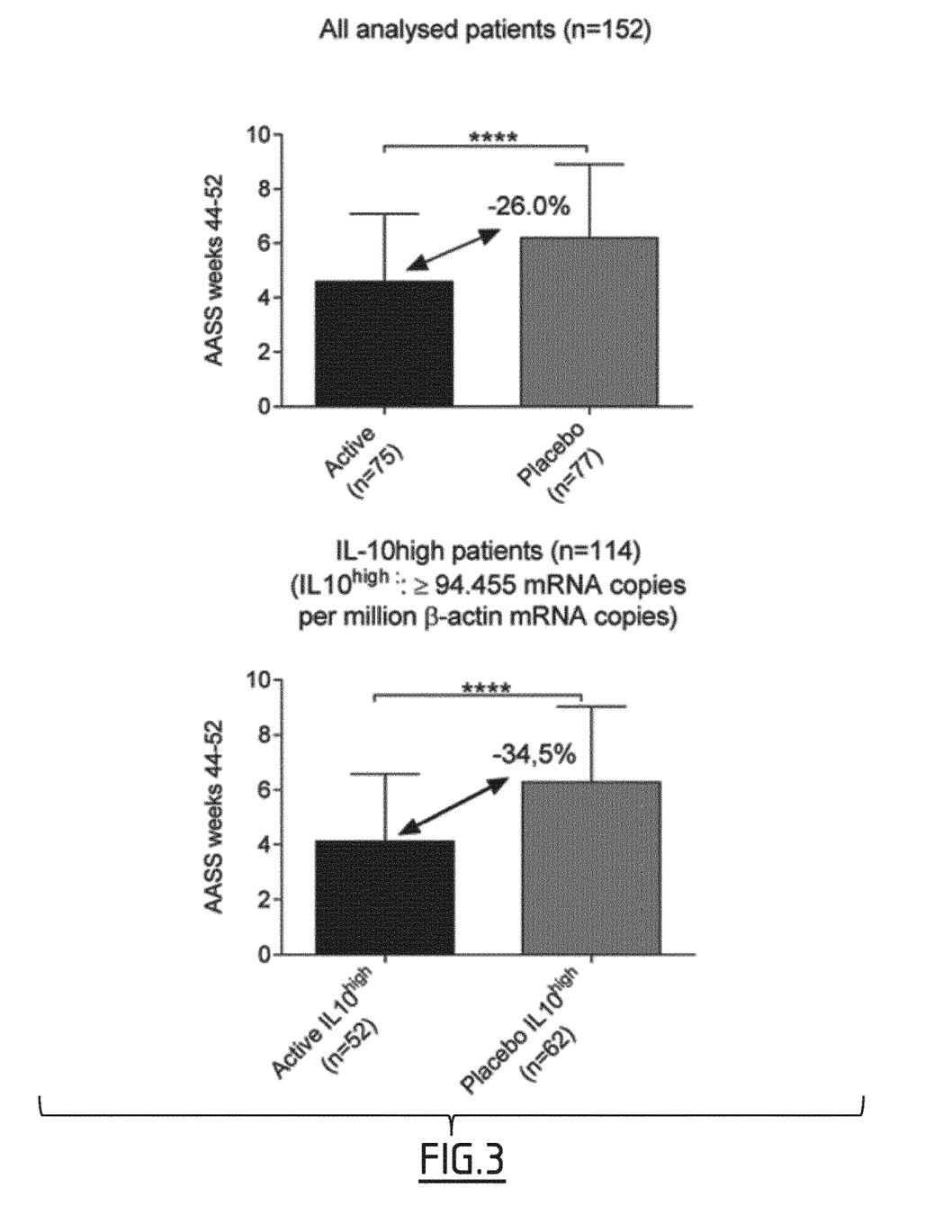
FIG. 3: Selection of IL-10 high patients improves the difference in clinical scores between active and placebo patients. Average Adjusted Symptom Scores (AASS; mean±SD) are presented after 12 months (weeks 44-52) of immunotherapy for 152 patients (75 receiving the active treatment and 77 receiving placebo) without using predictive biomarker criteria (upper panel). AASS are presented after 12 months (weeks 44-52) of immunotherapy for 114 patients exhibiting high levels of IL-10 mRNA (52 receiving the active treatment and 62 receiving placebo) (lower panel). (**** $P<0.0001$, Mann-Whitney tests).

To assess the advantage of selecting HDM allergic patients eligible to AIT based on IL-10 mRNA levels in whole blood cells, we selected for further analyses 75% (114 out of 152) of HDM allergic patients exhibiting the highest levels of IL-10 mRNA, defined as IL-10$^{high}$ patients based on copy numbers of IL-10 mRNA per million copies of β-actin mRNA ≥94.455. By contrast, 25% (38 out of 152) of patient exhibiting the lowest levels of IL-10 mRNA (IL-10$^{low}$ patients) were withdrawn from analyses. As shown in FIG. 3, after 12-month AIT (weeks 44-52), differences in AASS in IL-10$^{high}$ patients receiving the active treatment versus placebo were much higher (lower panel; −34.5%) when compared to differences in AASS in the whole cohort of unselected patients (upper panel; −26.0%).

The present study thus clearly establishes that the IL-10 gene is more expressed in whole blood cells from ARs relative to ANRs. These results provide for the use of IL-10 levels, in particular IL-10 mRNA levels, before AIT as a criterion to select patients more likely to benefit for treatment. As such, IL-10 represents a biomarker for predicting AIT efficacy.

Figure 4:
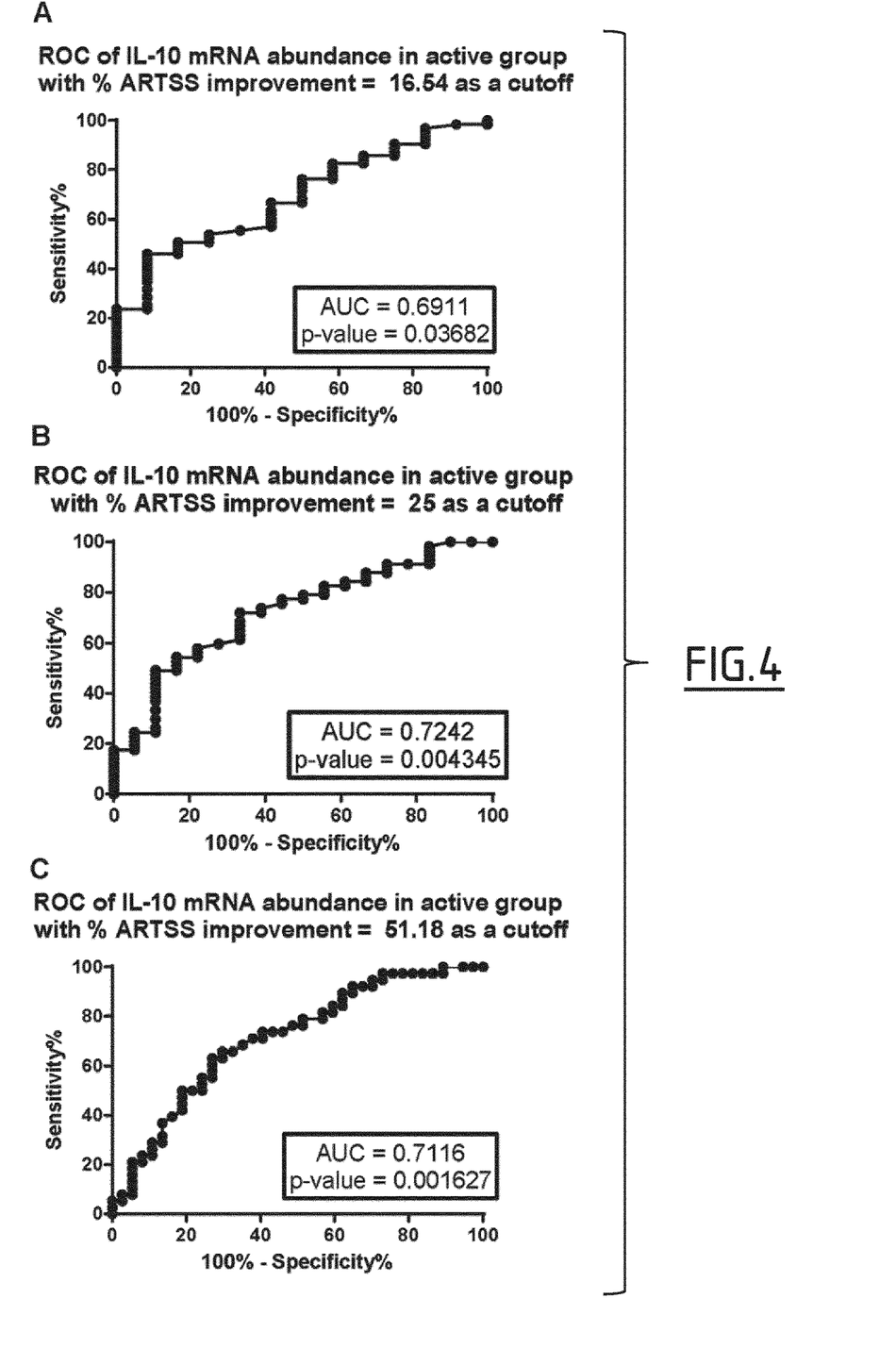

The pertinence of the IL-10 mRNA was further assessed by a receiver operating characteristic (ROC) analysis. The ROC curve of IL-10 mRNA copies levels of 75 active patients divided in 2 subgroups based on a threshold percentage of improvement in AASS of 16.54% is shown in FIG. 4A. The AUC was of 0.6911 (with p-value of 0.03682).

The ROC curve of IL-10 mRNA copies levels of 75 active patients divided in 2 subgroups based on a threshold percentage of improvement in AASS of 25% is shown in FIG. 4B. The AUC was of 0.7242 (with p-value of 0.004345).

The ROC curve of IL-10 mRNA copies levels of 75 active patients divided in 2 subgroups based on a threshold percentage of improvement in AASS of 51.18% is shown in FIG. 4C. The AUC was of 0.7116 (with p-value of 0.001627).

In these ROC curves, controls are defined as non-responder patients (i.e. patients with a percentage of improvement in AASS lower than the percentage of AASS improvement thresholds defined above).

These latter ROC curves in which the controls are defined as non-responder patients were associated with the following data on sensitivity and specificity.

TABLE 1

Threshold at 16.54% improvement in AASS
(IL-10 mRNA copies per million β-actin mRNA copies)

| Cutoff IL-10 | Sensitivity % | Specificity % |
|---|---|---|
| >47.10 | 98.41 | 0 |
| >51.00 | 98.41 | 8.333 |
| >53.15 | 96.83 | 16.67 |
| >55.05 | 95.24 | 16.67 |
| >57.35 | 93.65 | 16.67 |
| >63.40 | 92.06 | 16.67 |
| >69.40 | 90.48 | 16.67 |
| >70.60 | 90.48 | 25 |
| >71.35 | 88.89 | 25 |
| >72.60 | 87.3 | 25 |
| >75.15 | 85.71 | 25 |
| >77.00 | 85.71 | 33.33 |
| >77.80 | 84.13 | 33.33 |
| >79.40 | 82.54 | 33.33 |
| >80.80 | 82.54 | 41.67 |
| >81.65 | 80.95 | 41.67 |
| >82.50 | 79.37 | 41.67 |
| >86.70 | 77.78 | 41.67 |
| >90.90 | 76.19 | 41.67 |
| >91.85 | 76.19 | 50 |
| >93.15 | 74.6 | 50 |
| >97.40 | 73.02 | 50 |
| >102.0 | 71.43 | 50 |
| >105.5 | 68.25 | 50 |
| >111.0 | 66.67 | 50 |
| >114.5 | 66.67 | 58.33 |
| >119.0 | 63.49 | 58.33 |
| >124.0 | 61.9 | 58.33 |
| >126.5 | 60.32 | 58.33 |
| >128.5 | 58.73 | 58.33 |
| >129.5 | 57.14 | 58.33 |
| >131.0 | 55.56 | 66.67 |
| >133.5 | 53.97 | 75 |
| >137.0 | 52.38 | 75 |
| >139.5 | 50.79 | 75 |

TABLE 1-continued

Threshold at 16.54% improvement in AASS
(IL-10 mRNA copies per million β-actin mRNA copies)

| Cutoff IL-10 | Sensitivity % | Specificity % |
|---|---|---|
| >144.0 | 50.79 | 83.33 |
| >150.0 | 49.21 | 83.33 |
| >152.5 | 47.62 | 83.33 |
| >156.5 | 46.03 | 83.33 |
| >160.5 | 46.03 | 91.67 |
| >164.0 | 44.44 | 91.67 |
| >171.5 | 42.86 | 91.67 |
| >178.5 | 41.27 | 91.67 |
| >182.5 | 39.68 | 91.67 |
| >191.0 | 38.1 | 91.67 |
| >199.0 | 36.51 | 91.67 |
| >205.5 | 34.92 | 91.67 |
| >215.5 | 31.75 | 91.67 |
| >221.5 | 28.57 | 91.67 |
| >226.0 | 25.4 | 91.67 |
| >242.0 | 23.81 | 91.67 |
| >255.5 | 23.81 | 100 |
| >258.0 | 22.22 | 100 |
| >262.5 | 20.63 | 100 |
| >272.5 | 19.05 | 100 |
| >282.0 | 17.46 | 100 |
| >286.0 | 15.87 | 100 |
| >291.0 | 14.29 | 100 |
| >311.5 | 12.7 | 100 |
| >331.5 | 11.11 | 100 |
| >356.0 | 9.524 | 100 |
| >417.0 | 7.937 | 100 |
| >457.5 | 6.349 | 100 |
| >463.5 | 4.762 | 100 |
| >485.0 | 3.175 | 100 |
| >543.5 | 1.587 | 100 |

TABLE 2

Threshold at 25% improvement in AASS
(IL-10 mRNA copies per million β-actin mRNA copies)

| Cutoff IL-10 | Sensitivity % | Specificity % |
|---|---|---|
| >47.10 | 100 | 5.556 |
| >51.00 | 100 | 11.11 |
| >53.15 | 98.25 | 16.67 |
| >55.05 | 96.49 | 16.67 |
| >57.35 | 94.74 | 16.67 |
| >63.40 | 92.98 | 16.67 |
| >69.40 | 91.23 | 16.67 |
| >70.60 | 91.23 | 22.22 |
| >71.35 | 91.23 | 27.78 |
| >72.60 | 89.47 | 27.78 |
| >75.15 | 87.72 | 27.78 |
| >77.00 | 87.72 | 33.33 |
| >77.80 | 85.96 | 33.33 |
| >79.40 | 84.21 | 33.33 |
| >80.80 | 84.21 | 38.89 |
| >81.65 | 82.46 | 38.89 |
| >82.50 | 82.46 | 44.44 |
| >86.70 | 80.7 | 44.44 |
| >90.90 | 78.95 | 44.44 |
| >91.85 | 78.95 | 50 |
| >93.15 | 77.19 | 50 |
| >97.40 | 77.19 | 55.56 |
| >102.0 | 75.44 | 55.56 |
| >105.5 | 73.68 | 61.11 |
| >111.0 | 71.93 | 61.11 |
| >114.5 | 71.93 | 66.67 |
| >119.0 | 68.42 | 66.67 |
| >124.0 | 66.67 | 66.67 |
| >126.5 | 64.91 | 66.67 |
| >128.5 | 63.16 | 66.67 |
| >129.5 | 61.4 | 66.67 |
| >131.0 | 59.65 | 72.22 |
| >133.5 | 57.89 | 77.78 |

TABLE 2-continued

Threshold at 25% improvement in AASS
(IL-10 mRNA copies per million β-actin mRNA copies)

| Cutoff IL-10 | Sensitivity % | Specificity % |
|---|---|---|
| >137.0 | 56.14 | 77.78 |
| >139.5 | 54.39 | 77.78 |
| >144.0 | 54.39 | 83.33 |
| >150.0 | 52.63 | 83.33 |
| >152.5 | 50.88 | 83.33 |
| >156.5 | 49.12 | 83.33 |
| >160.5 | 49.12 | 88.89 |
| >164.0 | 47.37 | 88.89 |
| >171.5 | 45.61 | 88.89 |
| >178.5 | 43.86 | 88.89 |
| >182.5 | 42.11 | 88.89 |
| >191.0 | 40.35 | 88.89 |
| >199.0 | 38.6 | 88.89 |
| >205.5 | 36.84 | 88.89 |
| >215.5 | 33.33 | 88.89 |
| >221.5 | 29.82 | 88.89 |
| >226.0 | 26.32 | 88.89 |
| >242.0 | 24.56 | 88.89 |
| >255.5 | 24.56 | 94.44 |
| >258.0 | 22.81 | 94.44 |
| >262.5 | 21.05 | 94.44 |
| >272.5 | 19.3 | 94.44 |
| >282.0 | 17.54 | 94.44 |
| >286.0 | 17.54 | 100 |
| >291.0 | 15.79 | 100 |
| >311.5 | 14.04 | 100 |
| >331.5 | 12.28 | 100 |
| >356.0 | 10.53 | 100 |
| >417.0 | 8.772 | 100 |
| >457.5 | 7.018 | 100 |
| >463.5 | 5.263 | 100 |
| >485.0 | 3.509 | 100 |
| >543.5 | 1.754 | 100 |

TABLE 3

Threshold at 51.18% improvement in AASS
(IL-10 mRNA copies per million β-actin mRNA copies)

| Cutoff | Sensitivity % | Specificity % |
|---|---|---|
| >47.10 | 100 | 2.703 |
| >51.00 | 100 | 5.405 |
| >53.15 | 100 | 10.81 |
| >55.05 | 97.37 | 10.81 |
| >57.35 | 97.37 | 13.51 |
| >63.40 | 97.37 | 16.22 |
| >69.40 | 97.37 | 18.92 |
| >70.60 | 97.37 | 21.62 |
| >71.35 | 97.37 | 24.32 |
| >72.60 | 97.37 | 27.03 |
| >75.15 | 94.74 | 27.03 |
| >77.00 | 94.74 | 29.73 |
| >77.80 | 92.11 | 29.73 |
| >79.40 | 92.11 | 32.43 |
| >80.80 | 92.11 | 35.14 |
| >81.65 | 89.47 | 35.14 |
| >82.50 | 89.47 | 37.84 |
| >86.70 | 86.84 | 37.84 |
| >90.90 | 84.21 | 37.84 |
| >91.85 | 84.21 | 40.54 |
| >93.15 | 81.58 | 40.54 |
| >97.40 | 81.58 | 43.24 |
| >102.0 | 78.95 | 43.24 |
| >105.5 | 78.95 | 48.65 |
| >111.0 | 76.32 | 48.65 |
| >114.5 | 76.32 | 51.35 |
| >119.0 | 73.68 | 54.05 |
| >124.0 | 73.68 | 56.76 |
| >126.5 | 73.68 | 59.46 |
| >128.5 | 71.05 | 59.46 |
| >129.5 | 71.05 | 62.16 |

TABLE 3-continued

Threshold at 51.18% improvement in AASS
(IL-10 mRNA copies per million β-actin mRNA copies)

| Cutoff | Sensitivity % | Specificity % |
|---|---|---|
| >131.0 | 68.42 | 64.86 |
| >133.5 | 65.79 | 67.57 |
| >137.0 | 65.79 | 70.27 |
| >139.5 | 63.16 | 70.27 |
| >144.0 | 63.16 | 72.97 |
| >150.0 | 60.53 | 72.97 |
| >152.5 | 57.89 | 72.97 |
| >156.5 | 55.26 | 72.97 |
| >160.5 | 55.26 | 75.68 |
| >164.0 | 52.63 | 75.68 |
| >171.5 | 50 | 75.68 |
| >178.5 | 50 | 78.38 |
| >182.5 | 50 | 81.08 |
| >191.0 | 47.37 | 81.08 |
| >199.0 | 44.74 | 81.08 |
| >205.5 | 42.11 | 81.08 |
| >215.5 | 39.47 | 83.78 |
| >221.5 | 36.84 | 86.49 |
| >226.0 | 31.58 | 86.49 |
| >242.0 | 28.95 | 86.49 |
| >255.5 | 28.95 | 89.19 |
| >258.0 | 26.32 | 89.19 |
| >262.5 | 23.68 | 89.19 |
| >272.5 | 23.68 | 91.89 |
| >282.0 | 21.05 | 91.89 |
| >286.0 | 21.05 | 94.59 |
| >291.0 | 18.42 | 94.59 |
| >311.5 | 15.79 | 94.59 |
| >331.5 | 13.16 | 94.59 |
| >356.0 | 10.53 | 94.59 |
| >417.0 | 7.895 | 94.59 |
| >457.5 | 7.895 | 97.3 |
| >463.5 | 5.263 | 97.3 |
| >485.0 | 5.263 | 100 |
| >543.5 | 2.632 | 100 |

These results confirm that IL-10 mRNA is useful to discriminate clinical responders from non-responders before AIT.

Example 3—Expression of the IL-10 in Fresh PBMCs

Expression of IL-10 gene can be assessed in human PBMCs by PCR.

Total RNAs were isolated from PBMCs using silica-based spin columns. Complementary DNAs were then synthesized using a reverse transcriptase enzyme and random hexamer primers. Quantification was finally carried out by quantitative real-time PCR using the TaqMan technology with primers and probes specific for the IL-10 gene. Relative gene expression was calculated using the ΔΔCt method.

Example 4—Expression of IL-10 in Restimulated PBMCs

Expression of IL-10 gene can be assessed in restimulated human PBMCs by PCR

PBMCs were restimulated in vitro with relevant allergens under controlled culture conditions. Total RNAs were subsequently isolated using a spin column-based method followed by a reverse transcription step to generate complementary DNAs. The IL-10 gene expression was further quantified by real-time PCR using specific primers and a Taqman probe. Results were expressed as relative quantity and evaluated using the ΔΔCt method.

Example 5—Abundance of IL-10 in Serum

Measure of IL-10 polypeptide abundance in serum with aptamers

Nucleic acid aptamers specific for IL-10 were used to quantify IL-10 concentration in serum using a DNA quantification technique such as microarrays. The quantification was performed following the subsequent method:
(i) Aptamer reagents attached to streptavidin beads bind to serum proteins
(ii) The proteins that are bound to their specific aptamer reagents are then biotinylated
(iii) The aptamer-protein complexes are released by photo-cleaving the linker, and non-specific aptamer-protein complexes are separated
(iv) Biotinylated proteins are bound to a second streptavidin bead
(v) Bound aptamer reagents are removed from their protein targets
(vi) Aptamer reagents are collected and denatured
(vii) Aptamer reagents are measured using standard DNA analysis techniques like microarrays.

The invention claimed is:

1. A method for immunotherapy of house dust mite allergy in a patient comprising:
   (i) selecting a patient for immunotherapy by implementing a method comprising:
      a) measuring abundance of IL-10 mRNA in a biological sample from said patient,
      b) comparing said abundance of IL-10 mRNA with a control,
      c) identifying said patient as likely to be a responder to immunotherapy when
         (c1) the abundance of IL-10 mRNA in the patient sample is equal to or greater than the level of expression in a control derived from a responder subject, or group of responder subjects, known to respond to said immunotherapy; or
         (c2) the abundance of IL-10 mRNA in the patient sample is greater than the level of expression in a control derived from a non-responder subject, or group of non-responder subjects; or
         (c3) the abundance of IL-10 mRNA in the patient sample is greater than the level of expression in a control derived from a randomly selected group of subjects; and
      wherein said biological sample is taken before the commencement of immunotherapy, and wherein said immunotherapy comprises administration of a house dust mite allergen to said patient in order to treat house dust mite allergy, and
   (ii) administering said house dust mite allergen to said patient identified as likely to be a responder to said immunotherapy.

2. The method according to claim 1, wherein a responder demonstrates at least 10% improvement in clinical symptoms of house dust mite allergy and a non-responder demonstrates less than 10% improvement in clinical symptoms of house dust mite allergy.

3. The method according to claim 1, wherein said IL-10 mRNA consists of the sequence SEQ ID NO: 1.

4. The method according to claim 1, wherein the immunotherapy comprises administration of said house dust mite allergen to a mucosal surface, or administration of allergen via a subcutaneous, transdermal, intralymphatic or epicutaneous route.

* * * * *

SEQUENCE LISTING

```
<160> NUMBER OF SEQ ID NOS: 4

<210> SEQ ID NO 1
<211> LENGTH: 1629
<212> TYPE: DNA
<213> ORGANISM: Homo sapiens

<400> SEQUENCE: 1
acacatcagg ggcttgctct tgcaaaacca aaccacaaga cagacttgca aaagaaggca      60
tgcacagctc agcactgctc tgttgcctgg tcctcctgac tggggtgagg gccagccag     120 gccagggcac ccagtctgag aacagctgca cccacttccc aggcaacctg cctaacatgc    180
ttcgagatct ccgagatgcc ttcagcagag tgaagacttt ctttcaaatg aaggatcagc    240
tggacaactt gttgttaaag gagtccttgc tggaggactt taagggttac ctgggttgcc    300
aagccttgtc tgagatgatc cagttttacc tggaggaggt gatgcccaa gctgagaacc    360 aagacccaga catcaaggcg catgtgaact ccctggggga gaacctgaag accctcaggc    420
```

```
tgaggctacg gcgctgtcat cgatttcttc cctgtgaaaa caagagcaag gccgtggagc    480
aggtgaagaa tgcctttaat aagctccaag agaaaggcat ctacaaagcc atgagtgagt    540
ttgacatctt catcaactac atagaagcct acatgacaat gaagatacga aactgagaca    600
tcagggtggc gactctatag actctaggac ataaattaga ggtctccaaa atcggatctg    660
gggctctggg atagctgacc cagccccttg agaaacctta ttgtacctct cttatagaat    720
atttattacc tctgatacct caaccccat ttctatttat ttactgagct tctctgtgaa     780
cgatttagaa agaagcccaa tattataatt tttttcaata tttattattt tcacctgttt    840
ttaagctgtt tccatagggt gacacactat ggtatttgag tgttttaaga taaattataa    900
gttacataag ggaggaaaaa aaatgttctt tggggagcca acagaagctt ccattccaag    960
cctgaccacg ctttctagct gttgagctgt tttccctgac ctccctctaa tttatcttgt   1020
ctctgggctt ggggcttcct aactgctaca aatactctta ggaagagaaa ccagggagcc   1080
cctttgatga ttaattcacc ttccagtgtc tcgagggat tccctaacc tcattcccca     1140 accacttcat tcttgaaagc tgtggccagc ttgttattta taacaaccta aatttggttc   1200
taggccgggc gcggtggctc acgcctgtaa tcccagcact tgggaggct gaggcgggtg    1260 gatcacttga ggtcaggagt tcctaaccag cctggtcaac atggtgaaac cccgtctcta   1320
ctaaaaatac aaaaattagc cgggcatggt ggcgcgcacc tgtaatccca gctacttggg   1380
aggctgaggc aagagaattg cttgaaccca ggagatggaa gttgcagtga gctgatatca   1440
tgcccctgta ctccagcctg ggtgacagag caagactctg tctcaaaaaa taaaaataaa   1500
aataaatttg gttctaatag aactcagttt taactgaaat ttattcaatt cctctgggaa   1560
tgttacattg tttgtctgtc ttcatagcag attttaattt tgaataaata aatgtatctt   1620
attcacatc                                                           1629

<210> SEQ ID NO 2
<211> LENGTH: 4892
<212> TYPE: DNA
<213> ORGANISM: Homo sapiens

<400> SEQUENCE: 2
acacatcagg ggcttgctct tgcaaaacca aaccacaaga cagacttgca aaagaaggca     60
tgcacagctc agcactgctc tgttgcctgg tcctcctgac tggggtgagg gccagcccag    120
gccagggcac ccagtctgag aacagctgca cccacttccc aggcaacctg cctaacatgc    180
ttcgagatct ccgagatgcc ttcagcagag tgaagacttt cttgtgtagt atgattcctt    240
cctgtccttt ctctcttcct gggactgcct gaactagaca ttctcctgga actataagaa    300
ccctcctcct gcgcctccac ctccatcccc aacacctatt cccccaaact taaattctta    360
agagaatcct agatcaagcc atgggtttgg tgagttaagc taagccagat gatacagtaa    420
atgtgcagga aacctgcctt ataaagtaaa tgcgttctct ctcgtgctga aaacttata     480 agatcctgct ggcgctctat actttattgg ctaggagaag taaagaaatg tctgattcga    540
ggtgaagatg ctccccatgc cttgcagcag ggaaatttaa attgcctctg cttagagcgt    600
ttccagacct gaaagaccag tggtttaggg aagcactcta catgagggaa acctgcatta    660
gaaggagctt cttaatccct gggatctttc caagctaaac tggatgtcta cagtggggag    720
aaagaaaagc agagaacagg acatgagggg ggctcaaggc cccgaagggt tgacataggt    780
gtcccttaaa gccgaatgta gctccgcaga aagaagacca ggactgagtc aagcttctgc    840
tttcccttca aaatcggcca gatttttaa ataacttgac tctgaggagg aggacctgat    900
```

```
ttaagtgatg gtcccatcac tgttgaatcc tctgttttta aaactcccct tttgatttt       960 ttgggccaga gccaatttta tttaaaaaaa aaaatctcta aatgaaaggg catcaaaaag      1020
accgcatttc agttatttcc ccaaacctca agttcattct cctttgttc ttcctgcagc       1080 aaatgaagga tcagctggac aacttgttgt taaaggagtc cttgctggag gactttaagg      1140
tgagagcagg ggcggggtgc tgggggagtg tgcagcatga ttaagggaag ggagactctg      1200
cttcctgatt gcagggaatt gggttgtgtt ccttcgcttt gaaaggaga agtgggaaga       1260 tgttaactca gcacatccag cagccagagg gtttacaaag gctcagtcc cttcggggag       1320 gcttctggtg aaggaggatc gctagaacca agctgtcctc ttaagctagt tgcagcagcc      1380
cctcctccca gccacctccg ccaatctctc actcacctt ggctcctgcc cttagggtta      1440
cctgggttgc caagccttgt ctgagatgat ccagttttac ctggaggagg tgatgcccca     1500
agctgagaac caagacccag acatcaaggc gcatgtgaac tccctggggg agaacctgaa      1560
gaccctcagg ctgaggctac ggcgctgtgt aagtagcaga tcagtttttt cccttgcagc      1620 tgccccaaa ataccatctc ctacagacca gcagggacac tcacatccac agacacagca      1680
aagacacaga ctggcagagc tagctgtaaa tgaggaaaga ctcctggagt cagatctctt     1740
gctcatttct ctttgagcag gcgttggggg tggctgctag gcatttacat gtgaaatttg     1800
caaacagctt tcctgttatt tgtgagtcat ttgtgggtta ttaactactc ccctctctct    1860
tcataaaagg agcccagagc ttcagtcagg cctccactgc ctctttgtaa ctagaccctg    1920
ggcggggagc taaggttccc aagcagagga aacatcattc acctctttta atctcaatgt    1980
tttgaaagca aagctctaag aagggcccaa ttgactgaca ggatttcccc tggcatttta    2040
gaagggacaa gggggctatt catccccagg ctagtgtcta tgagtaattc ctccaggtaa    2100 ttttatttctc caactgaaat gatgccctca ctactaatgg tttccctgt tctgtcacca    2160 atattggaaa atcagttggt gtctatttgt aggacaaggc tatgtgaagg gtttggtccc     2220
agtagcttcc ctcctcagat gcttagaagt gttcctcggt ggctgtgact gacggggagg     2280
aacaggagag agaggcagaa aaggacaggc tgaagaatgc ctcgctcagc actgcaggag     2340
atactgtaga gttctggggg aggaaggaat cccaagacct gggttgtcat ccaagccttg     2400
caaacatctt ggagtgagtc ctggagaaat acatttaact cccagggcca tggaagcagg     2460
gctcagttct ctctgggagc tgtgaggcaa ggcatttgga taaatctggc ctcctcatga     2520
tgccaccagc ttgtcccta agtgtgatgg acatggagct ggaagccagg atcaccaaca     2580 cttttctcttt tcttccacag catcgatttc ttccctgtga aaacaagagc aaggccgtgg    2640
agcaggtgaa gaatgccttt aataaggtga gcttggatgg tggcagagag ggtctgcaga     2700
gcacaaccca tgcccactcc ccaaccccaa agcatggaag gtggtgggga ctcaataggc     2760
cccattcttc attggagaga gtgtgggaac ctgacagatg gtatgacctg ctcagccagt    2820
gaggagctgc tgccttgatt gtatttgttt tctgttaagt gtctttgggg gtttctaaat     2880
gactgctcgc tgcctttgca ggcttgcggg ttaggctggc cggccagcct gtgaacacag     2940
tgagctgcat gctggggaga gtgacaaagg aaacagaaag tacagaaagt agcttgttgg     3000
gaatctaggc tgaacccaca cgtgcaggaa gctggcacat aaatgtgcac atacaaatac    3060
acctgggggt tcagcccaga ctcccccagaa ctcagaatga gcaggaagct ggattctcac    3120
ttaacctgga gttggttcaa gcccgctttc catctgccct tcgcacctgc ggaggtgcct     3180
gagaatgtca gttcccaaac gaaatggggt ttcacacttc caactgtgcg tgaactttt      3240
```

| | |
|---|---|
| cagtctgatt tcccagaaac cgtgcggcct atgtcctcct cgtgggctgg ggacagacac | 3300 |
| tgcacagagt gccaacatca gggggtgtga atttctcata gtaggtcagg gcggcagggc | 3360 |
| agggcctgct cagtgtgttg gtgggagaac acagacattt aaaaggctcc ctcctctcct | 3420 |
| ctcaccgtct tgctttcgaa gcgcttcctc taatgtcttt tcatcaaact ctgcataatc | 3480 |
| atcatgtgaa tacgtgacct ttaaaattgt tgaaaaggca tcattttgaa gacagtgctt | 3540 |
| tgcaaaatga atgctcccct tgctaggggg aggcctggag gagatgaagg tcaatgcaca | 3600 |
| gcctttccca aggcagctag gcctatcctc tggtttactt cccagcgtga gggagaacaa | 3660 |
| gcaacctctg cactcaaggt catgcccatc catgagcatg agggagggga gcctatttag | 3720 |
| tccccagaaa ggattttaac tgtatgtttc ttatctctct gcacagctcc aagagaaagg | 3780 |
| catctcacaa gccatgagtg agtttgacat cttcatcaac tacatagaag cctacatgac | 3840 |
| aatgaagata cgaaactgag acatcagggt ggcgactcta tagactctag gacataaatt | 3900 |
| agaggtctcc aaaatcggat ctggggctct gggatagctg acccagcccc ttgagaaacc | 3960 |
| ttattgtacc tctcttatag aatatttatt acctctgata cctcaacccc catttctatt | 4020 |
| tatttactga gcttctctgt gaacgattta gaaagaagcc caatattata atttttttca | 4080 |
| atatttatta ttttcacctg tttttaagct gtttccatag ggtgacacac tatggtattt | 4140 |
| gagtgtttta agataaatta taagttacat aagggaggaa aaaaaatgtt ctttggggag | 4200 |
| ccaacagaag cttccattcc aagcctgacc acgctttcta gctgttgagc tgttttccct | 4260 |
| gacctccctc taatttatct tgtctctggg cttggggctt cctaactgct acaaatactc | 4320 |
| ttaggaagag aaaccaggga gcccctttga tgattaattc accttccagt gtctcggagg | 4380 |
| gattccccta acctcattcc ccaaccactt cattcttgaa agctgtggcc agcttgttat | 4440 |
| ttataacaac ctaaatttgg ttctaggccg ggcgcggtgg ctcacgcctg taatcccagc | 4500 |
| actttgggag gctgaggcgg gtggatcact tgaggtcagg agttcctaac cagcctggtc | 4560 |
| aacatggtga aacccgtctc tactaaaaaa tacaaaaatt agccgggcat ggtggcgcgc | 4620 |
| acctgtaatc ccagctactt gggaggctga ggcaagagaa ttgcttgaac ccaggagatg | 4680 |
| gaagttgcag tgagctgata tcatgcccct gtactccagc ctgggtgaca gagcaagact | 4740 |
| ctgtctcaaa aaataaaaat aaaaataaat ttggttctaa tagaactcag ttttaactag | 4800 |
| aatttattca attcctctgg gaatgttaca ttgtttgtct gtcttcatag cagattttaa | 4860 |
| ttttgaataa ataaatgtat cttattcaca tc | 4892 |

<210> SEQ ID NO 3
<211> LENGTH: 178
<212> TYPE: PRT
<213> ORGANISM: Homo sapiens

<400> SEQUENCE: 3

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

```
Gln Ala Leu Ser Glu Met Ile Gln Phe Tyr Leu Glu Glu Val Met Pro
                85                  90                  95
Gln Ala Glu Asn Gln Asp Pro Asp Ile Lys Ala His Val Asn Ser Leu
            100                 105                 110
Gly Glu Asn Leu Lys Thr Leu Arg Leu Arg Leu Arg Arg Cys His Arg
            115                 120                 125
Phe Leu Pro Cys Glu Asn Lys Ser Lys Ala Val Glu Gln Val Lys Asn
        130                 135                 140
Ala Phe Asn Lys Leu Gln Glu Lys Gly Ile Tyr Lys Ala Met Ser Glu
145                 150                 155                 160
Phe Asp Ile Phe Ile Asn Tyr Ile Glu Ala Tyr Met Thr Met Lys Ile
                165                 170                 175
Arg Asn

<210> SEQ ID NO 4
<211> LENGTH: 160
<212> TYPE: PRT
<213> ORGANISM: Homo sapiens

<400> SEQUENCE: 4

Ser Pro Gly Gln Gly Thr Gln Ser Glu Asn Ser Cys Thr His Phe Pro
1               5                   10                  15
Gly Asn Leu Pro Asn Met Leu Arg Asp Leu Arg Asp Ala Phe Ser Arg
            20                  25                  30
Val Lys Thr Phe Phe Gln Met Lys Asp Gln Leu Asp Asn Leu Leu Leu
        35                  40                  45
Lys Glu Ser Leu Leu Glu Asp Phe Lys Gly Tyr Leu Gly Cys Gln Ala
    50                  55                  60
Leu Ser Glu Met Ile Gln Phe Tyr Leu Glu Glu Val Met Pro Gln Ala
65                  70                  75                  80
Glu Asn Gln Asp Pro Asp Ile Lys Ala His Val Asn Ser Leu Gly Glu
                85                  90                  95
Asn Leu Lys Thr Leu Arg Leu Arg Leu Arg Arg Cys His Arg Phe Leu
            100                 105                 110
Pro Cys Glu Asn Lys Ser Lys Ala Val Glu Gln Val Lys Asn Ala Phe
        115                 120                 125
Asn Lys Leu Gln Glu Lys Gly Ile Tyr Lys Ala Met Ser Glu Phe Asp
    130                 135                 140
Ile Phe Ile Asn Tyr Ile Glu Ala Tyr Met Thr Met Lys Ile Arg Asn
145                 150                 155                 160
```